United States Patent [19]
Silver et al.

[11] Patent Number: 5,632,725
[45] Date of Patent: May 27, 1997

[54] POLYCENTRIC VARIABLE AXIS HINGE FOR AN ORTHOPEDIC KNEE BRACE

[75] Inventors: Daniel M. Silver, Los Angeles; Russell A. Rothenberg, Santa Monica, both of Calif.

[73] Assignee: S.R. Orthopedic Laboratories, Inc., Santa Monica, Calif.

[21] Appl. No.: 368,021

[22] Filed: Jan. 3, 1995

[51] Int. Cl.⁶ .................................................. A61F 5/01
[52] U.S. Cl. ................................ 602/26; 602/16; 623/39
[58] Field of Search .................................................. 602/26

[56] References Cited

U.S. PATENT DOCUMENTS

| | | | |
|---|---|---|---|
| 4,379,463 | 4/1983 | Meier et al. | 602/26 X |
| 4,723,539 | 2/1988 | Townsend. | |
| 4,773,404 | 9/1988 | Townsend. | |
| 4,890,607 | 1/1990 | Townsend. | |
| 5,060,640 | 10/1991 | Rasmusson | 602/26 X |
| 5,230,696 | 7/1993 | Silver et al. | |

Primary Examiner—Richard J. Apley
Assistant Examiner—David R. Risley

[57] ABSTRACT

A polycentric variable axis hinge for use in an orthopedic knee brace to provide a mechanical joint between the femoral and tibial cuffs of the brace. The hinge includes a femoral stem which is attached to the femoral cuff and which extends downwardly from the femoral cuff, and it also includes a tibial stem attached to the tibial cuff which extends upwardly from the tibial cuff. The ends of the two stems overlap one another to provide a joint. The action is such that angular movement of the stems relative to one another causes them to slide and rotate relative to one another to replicate the actual movement of the knee joint of the user as the leg is bent and straightened. The femoral and tibial stems have a 30 degree angulated shape so as to displace the joint of the hinge two-thirds of the distance from the patella to the rear of the knee to cause the hinge precisely to simulate the anatomical femoral arc in the human knee. The hinge is constructed to be relatively thin as compared to the prior art hinges and to be relatively light so as to optimize the comfort of the wearer. The hinge is also rugged in its construction.

6 Claims, 2 Drawing Sheets

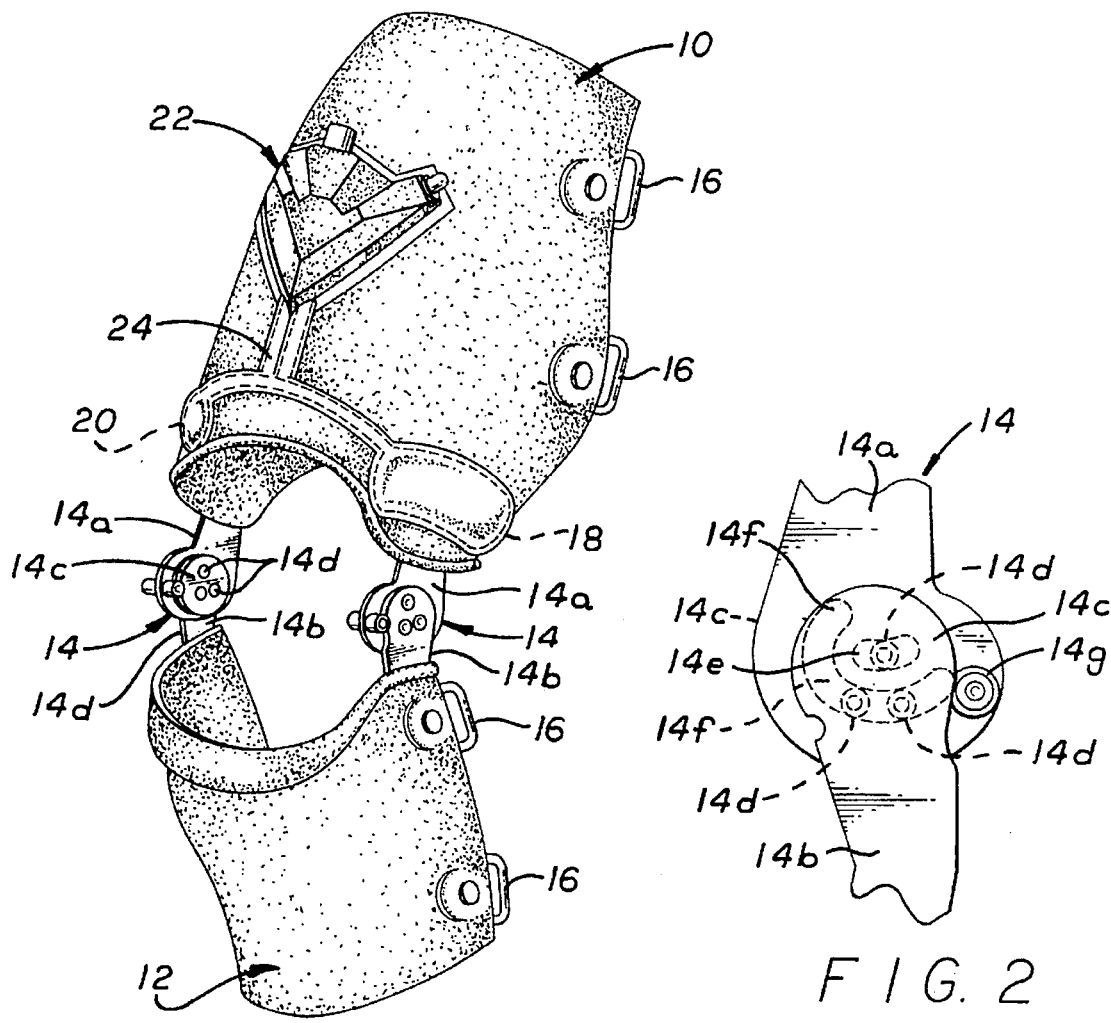
FIG. 1
FIG. 2
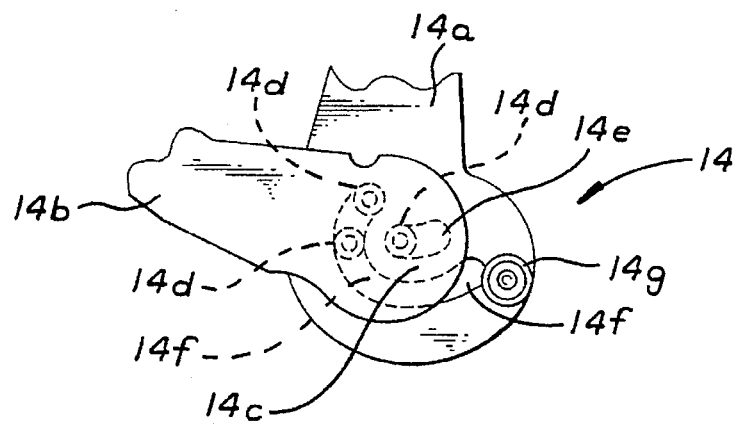
FIG. 3

POLYCENTRIC VARIABLE AXIS HINGE FOR AN ORTHOPEDIC KNEE BRACE

BACKGROUND OF THE INVENTION

The present invention relates to a polycentric variable axis hinge for use. in particular, but not exclusively, in conjunction with orthopedic knee braces of the type intended to reinforce an injured knee joint. The hinge of the present invention constitutes an improvement over the hinge described and claimed in U.S. Pat. No. 5,230,696 which issued Jul. 27, 1993.

As pointed out in that patent, the human knee is acknowledged as one of the weakest joints in the body. It is the articulating joint between the thigh and calf muscle groups, and it supports the weight of the body while a person is walking or running. The joint is held together by two small but strong ligaments, namely, the anterior and posterior cruciate ligaments. Knee instability arising out of cartilage damage, the ligament strain and other causes is relatively commonplace since the knee joint is subjected to significant loads during the course of almost any kind of physical activity requiring the use of the legs.

The thigh and legs of the human body are joined to each other through the knee joint, and the principal motions of the knee joint are extension and flexion due to rotation about a horizontal axis extending across the knee joint in a medial-lateral direction. These motions are complex because they take place about a rotational axis which is not fixed, as is the case with the elbow, but which shifts slightly across the knee joint in the anterior-posterior direction. It is important for an adequate knee brace to follow the shifting path of the rotational axis of the knee as closely as possible, and accordingly the principal objective of the present invention is to provide a knee brace hinge which is capable of fulfilling such a criterion.

Additionally, and particularly in the case of injured or weak knees, means must be provided in the knee brace hinge to control the extension of the knee joint and to stop the extension, for example, short of 15%–5% of full extension, in order to prevent knee ligament injuries. Another objective of the invention is to provide a knee brace hinge which incorporates improved stop means that may be adjustable to tailor ,the hinge to individuals, to control the extension of the knee joint, and to stop the extension at a predetermined degree of full extension.

In U.S. Pat. No. 4,773,404, and in its parent U.S. Pat. No. 4,723,539, and in U.S. Pat. No. 4,890,607, multi-axis controlled motion knee hinges are disclosed. Each hinge is constructed to enable the tibia to slide rearwardly relative to the femur for a predetermined distance throughout an initial range of flexion of the knee from a straight leg position, and beyond that initial range of flexion, to rotate relative to the femur along a predetermined arcuate path.

In the construction of the hinge described in U.S. Pat. No. 4,890,607, the end portions of femur and tibia are interconnected by a cam assembly comprised of a pair of cam slots in one of the links of the hinge, and cam follower pins mounted on the other link and engaging the slots. In the particular construction described in U.S. Pat. No. 4,890,607, each slot has a straight segment adjoining an arcuate segment of equal radius.

The variable axis hinge of the present invention is of the same general type as the hinge disclosed in U.S. Pat. No. 5,230,696 and in U.S. Pat. No. 4,890,607, but it is constructed in a manner such that the hinge more closely follows the actual movement of the knee, as the leg is bent in the rearward direction.

The hinges described in U.S. Pat. Nos. 5,230,696 and 4,890,607 each comprises a knee brace hinge mechanism which utilizes first and second variable radii camming slots and corresponding cam pin followers. One of the camming slots serves to provide the anterior motion of the upper link of the hinge, while the second camming slot provides for the unicentric phase of the hinge artarokinematics. During the initial range of motion, pivoting occurs through a short multi-radii slot segment about one of the cam pin followers disposed within that slot. After that cam pin follower reaches the anterior end of the slot, it serves as a pivot for movement of the other cam pin followers along the second variable radii slot.

When hinges of the type being discussed are used in conjunction with orthopedic knee braces, they provide a polycentric mechanical joint between the femoral and tibial cuffs of the brace. For that application, the hinge includes a femoral stem which is attached to the femoral cuff and which extends downwardly from the femoral cuff, and it also includes a tibial stem attached to the tibial cuff and which extends upwardly from the tibial cuff. The action of the hinge is such that angular movements of the stems relative to one another cause them to slide and rotate relative to one another so as to replicate the actual movement of the knee joint of the user as the leg is bent and straightened.

The hinge of the present invention is constructed in a manner such that the femoral and tibial stems are angulated so as to position the axes of rotation of the hinge of the order of two-thirds of the distance from the patella to the rear of the patient's knee in order to locate the axes of rotation of the hinge in a position in which the hinge precisely simulates the anatomical femoral arc in the human knee.

The hinge of the invention is also constructed to be relatively thin as compared with the hinge described in U.S. Pat. No. 5,230,696, and it is rugged in its construction and relatively light and comfortable insofar as the patient is concerned.

Accordingly, a general objective of the present invention is to provide an improved multi-axis hinge for an orthopedic knee brace which is constructed to have the ability accurately to replicate the complex movements of the knee of the patient, as the leg is bent and straightened.

Another objective of the invention is to provide such a multi-axis hinge which is light in weight and which has relatively high integral strength, as well as tolerance precision and production efficiency.

Yet another objective of the invention is to provide such a variable axis orthopedic knee brace hinge which is constructed in a manner so as to render the knee brace in which it is mounted comfortable to the wearer.

BRIEF DESCRIPTION OF THE DRAWINGS

FIG. 1 is a perspective representation of a portion of an orthopedic knee brace which includes an upper (femoral) anterior cuff and lower (tibial) anterior cuff; the upper and lower cuffs being hinged together by a pair of polycentric variable axis hinges constructed in accordance with the concepts of the present invention;

FIG. 2 is a schematic representation of a polycentric variable axis hinge which may be constructed to incorporate the concepts of the invention, showing the position of the hinge when the leg of the knee brace wearer is fully extended;

FIG. 3 is a schematic representation of the hinge of FIG. 2, showing the position of the hinge when the leg of knee brace wearer is bent to an extreme bent position;

DETAILED DESCRIPTION OF THE ILLUSTRATED EMBODIMENT

Figure 4:
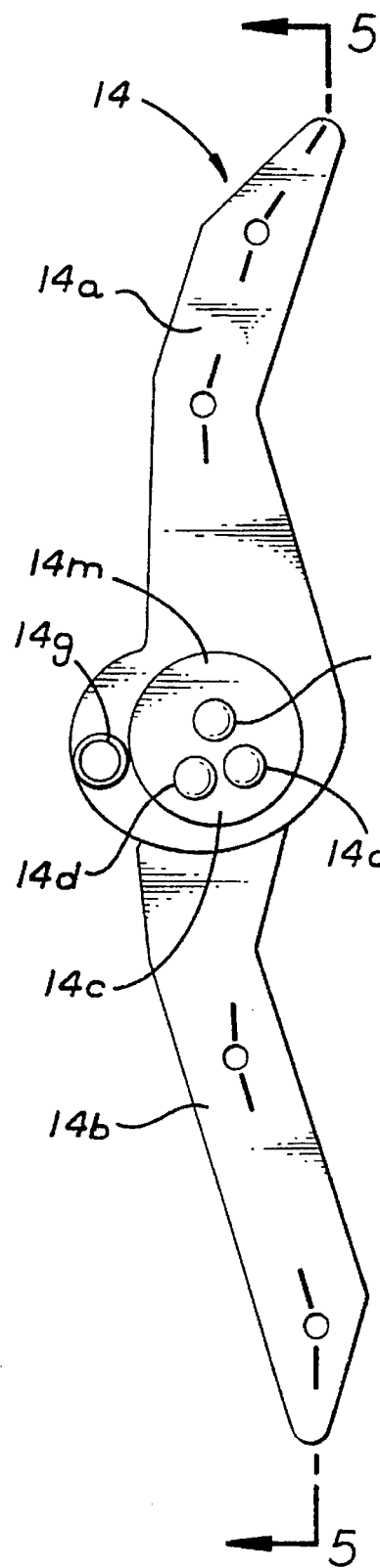
FIG. 4 is a plan view of the femoral and tibial stems of the hinge of the invention and of the structure which couples the two stems together, the stems have an angled configuration in accordance with the concepts of the invention.

As stated above, FIG. 1 is a perspective representation of a portion of an orthopedic knee brace which includes an upper anterior cuff 10 which engages the thigh of the wearer, and a lower anterior cuff 12 which engages the leg of the wearer below the knee. The upper and lower cuffs are hinged to one another by a pair of hinges 14 which, as stated, are constructed to incorporate the concepts of the present invention.

In the embodiment shown in FIG. 1, a pair of air pillows 18 and 20 are interposed between the lower edge of cuff 10 and the thigh of the wearer in accordance with the concepts described in U.S. Pat. No. 5,230,696. As described in U.S. Pat. No. 5,230,696, the air pillows may be inflated by a miniature air pump 22 mounted on cuff 10 which enables the wearer, by repeatedly depressing and releasing the resilient top of the pump, to introduce pressurized air into the air pillows through a tube 24 to inflate the air pillows. The air pillows are constructed and positioned to prevent the upper cuff 10 from sliding downwardly along the thigh of the patient. The cuffs 10 and 12 may be held in place on a patient by appropriate straps received in loop fittings 16.

Details of the central portion of the hinge 14 are shown in FIGS. 2 and 3. As shown, in FIGS. 4–6, each hinge includes a planar femoral steam 14a which is securely jointed to the femoral cuff 10 so as to extend downwardly therefrom. Each hinge also includes a planar tibial stem 14b which is securely attached to the tibial cuff 12 so as to extend upwardly from the tibial cuff.

Any known means for joining the stems 14a and 14b to their respective cuffs may be utilized, such as laminating or sewing the stems into the cuffs. As can be seen from FIG. 1, the femoral and tibial stems 14a, 14b extend essentially parallel to each other and are positioned so that the distal ends thereof overlap to create a mechanical pivotal hinge mechanism 14c.

Figure 5:
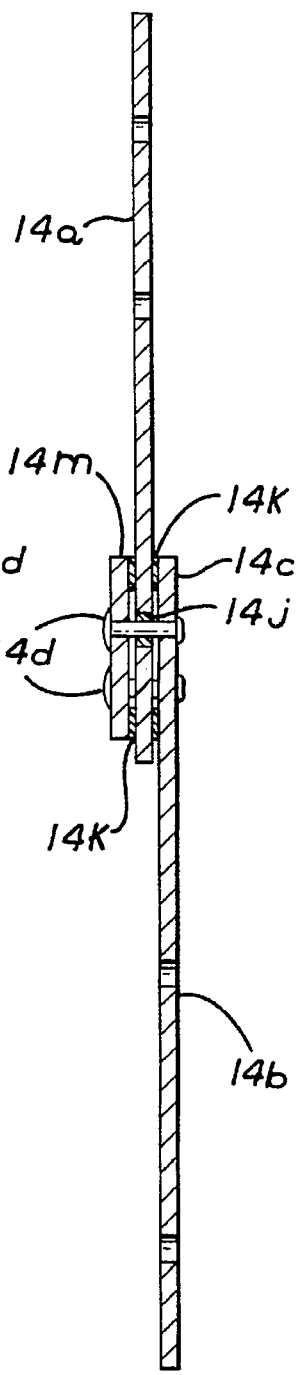
FIG. 5 is a section of the hinge taken essentially along the line 5—5 of FIG. 4.
Figure 6:
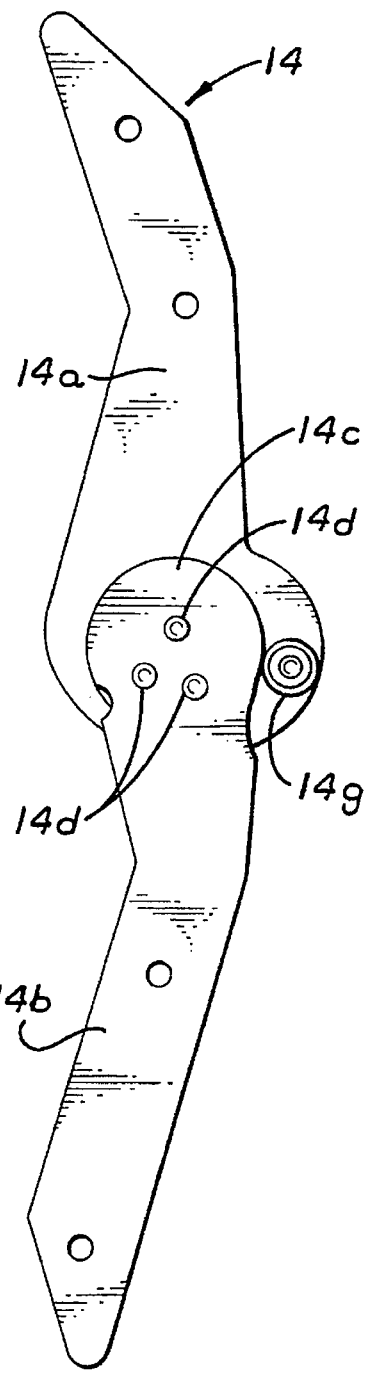
FIG. 6 is another view of the hinge of FIG. 4 taken from the opposite side.

The stems 14a and 14b are shown in their entirety in FIGS. 4, 5 and 6. As shown in FIGS. 4 and 5, for example, each of the stems 14a and 14b has an angled configuration defining, for example, an angle of the order of 30°, as shown in FIGS. 4 and 6 forming a uni-planar angled configuration. The purpose of the angled configuration of the stems is to displace the hinge mechanism 14c to the rear of the knee of the wearer when the leg of the wearer is fully extended so as to position the initial location of the pivot axes of the hinge approximately two-thirds of the distance from the anterior of the patella to the back of each knee.

As can be seen from FIG. 1, the femoral and tibial stems 14a, 14b extend essentially parallel to one another and they are positioned so that the distal ends thereof overlap to create the mechanical pivotal hinge mechanism 14c. As shown in FIGS. 2–6, the hinge mechanism includes three bearing pins 14d. These bearing pins are in the form of rivets extending through the end of the tibial stem 14b, and extending through slots 14e and 14f in the end of the femoral stem 14a. The three bearing pins 14d are each surrounded by a ceramic bearing sleeve 14j (FIG. 5).

Slot 14e is positioned within the confines of slot 14f. The slots 14e and 14f also have variable radii so that angular and lateral movements of the stems 14a and 14b may be realized which precisely follow the angular movements of the femur and tibia of the cuff wearer. As shown, one of the bearing pins 14d is received in the upper slot 14e, and two of the bearing pins 14d are received in the lower slot 14f. The three bearing pins 14d are positioned on the end of the tibial stem 14b to form an isosceles triangle, as best shown in FIGS. 2, 3, 4 and 6.

The bearing pins 14d function as cam followers in the slots 14e and 14f. A disc-shaped cover 14m (FIGS. 4 and 5) is held in place by the pins 14d to sandwich the femoral stem 14a between the cover 14m and the tibial stem 14b. The cover 14m is removed in FIGS. 1–3 for purposes of illustrating the other component parts. Annular-shaped ceramic bearings 14k (FIG. 5) are interposed between the cover 14m and end of femoral stem 14a, and between the end of femoral stem 14a and the end of tibial stem 14b, respectively.

It will be observed that as the tibial stem 14b is turned from the fully extended position of FIG. 2 to the bent position of FIG. 3, the upper bearing pin 14d moves in the variable radii slot 14e to one end of the slot. During such movement, the tibial stem is displaced in the posterior direction with respect to the femoral stem. When the upper bearing pin 14d reaches the end of the variable radii slot 14e, as shown in FIG. 3, the tibial stem rotates about the axis of the upper bearing pin 14d until it reaches the extreme bent position shown in FIG. 3. When in the illustrated extreme bent position, the lefthand lower bearing pin 14d engages the opposite end of the variable radial slot 14f.

Accordingly, as the knee brace wearer's leg is bent about the knee, the tibial and femoral stems 14b and 14a slide and rotate in a manner to precisely replicate the action of the wearer's knee joint.

A two-piece stop FIGS. 4 and 6 is attached to the end of the femoral stem 14a to be engaged by the edge of the cover 14m (FIG. 4) and by the edge of the end of the tibial stem 14b (FIG. 6) which has a circular configuration, when the leg of the wearer is fully extended. The stop 14g is provided with a rubber bushing so as to form a soft cushion stop for the mechanism when the leg is fully extended. The stop 14g may be removable, and it may be replaced by stops of different sizes when it is desired to tailor the hinge to the requirements of different users.

The invention provides, therefore, an improved polycentric variable axis hinge for an orthopedic knee brace which is constructed to follow precisely the movements of the wearer's knee as the leg is bent and straightened.

While a particular embodiment of the invention has been shown and described, modifications may be made, and it is intended in the following claims to cover all such modifications which fall within the true spirit and scope of the invention.

We claim:

1. A polycentric variable axis hinge for use in an orthopedic knee brace providing a mechanical joint between the femoral and tibial cuffs of the brace, said hinge including a planar femoral stem attached to the femoral cuff and extending downwardly therefrom and a planar tibial stem attached to the tibial cuff and extending upwardly therefrom, the distal ends of the stems overlapping one another to provide a joint, a plurality of bearing pins extending through said joint for securing said femoral and tibial cuffs together and forming bearings for said joint, and each of the stems having a selected uni-planar angled configuration, with the end portions of each planar stem defining an angle of the order of 30° with respect to one another so as to cause said joint to be displaced posteriorly from the patella of the knee of the cuff wearer toward the back of the knee by a predetermined amount.

2. The polycentric variable axis hinge defined in claim 1, in which said bearing pins have the form of rivets, each encased in a bearing sleeve.

3. The polycentric variable axis hinge defined in claim 1, and which includes an annular bearing member mounted at said joint and interposed between said distal ends of the femoral and tibial stems; a disc-shaped cover member mounted on the outer side of said distal end of said femoral stem coaxially with said annular bearing member; and a second annular bearing member mounted coaxially with said cover and with said first bearing member between said cover and said femoral stem.

4. The polycentric variable axis hinge defined in claim 3, and which includes a split stop member mounted on said distal end of said tibial stem to be engaged by the edges of the cover and of said distal end of said femoral stem when the leg of the knee brace wearer is extended with said stop serving to limit the extension angle of the leg.

5. The polycentric variable axis hinge defined in claim 4, in which said stop member includes resilient bushings to be engaged by the edge of the femoral stem and of the cover to provide a soft stop action.

6. The polycentric variable axis hinge defined in claim 4 in which said stop is removable to be replaced by other stops of different sizes.

* * * * *